(12) United States Patent
Chen et al.

(10) Patent No.: US 11,124,517 B2
(45) Date of Patent: Sep. 21, 2021

(54) CRYSTAL FORM OF BARICITINIB AND PREPARATION METHOD THEREOF

(71) Applicant: CRYSTAL PHARMACEUTICAL (SUZHOU) CO., LTD., Jiangsu (CN)

(72) Inventors: Minhua Chen, Jiangsu (CN); Yanfeng Zhang, Jiangsu (CN); Qiyue Liu, Jiangsu (CN); Xiaoyu Zhang, Jiangsu (CN)

(73) Assignee: CRYSTAL PHARMACEUTICAL (SUZHOU) CO., LTD.

( * ) Notice: Subject to any disclaimer, the term of this patent is extended or adjusted under 35 U.S.C. 154(b) by 79 days.

(21) Appl. No.: 16/625,758

(22) PCT Filed: May 23, 2018

(86) PCT No.: PCT/CN2018/088068
§ 371 (c)(1),
(2) Date: Dec. 22, 2019

(87) PCT Pub. No.: WO2018/233437
PCT Pub. Date: Dec. 27, 2018

(65) Prior Publication Data
US 2021/0147423 A1 May 20, 2021

(30) Foreign Application Priority Data
Jun. 22, 2017 (CN) .......................... 201710479111.9

(51) Int. Cl.
*A61K 31/519* (2006.01)
*C07D 487/04* (2006.01)

(52) U.S. Cl.
CPC ........ *C07D 487/04* (2013.01); *C07B 2200/13* (2013.01)

(58) Field of Classification Search
CPC ........................... A61K 31/519; C07D 487/04
USPC ........................................ 514/265.1; 544/280
See application file for complete search history.

*Primary Examiner* — Douglas M Willis
(74) *Attorney, Agent, or Firm* — Enshan Hong; VLP Law Group LLP (57) ABSTRACT

The present disclosure relates to crystalline forms of Baricitinib and processes for preparation thereof. The present disclosure also relates to pharmaceutical composition containing these crystalline forms and use of these crystalline forms for preparing JAK inhibitor drugs and preparing drugs treating rheumatoid arthritis. The crystalline forms of the present disclosure have one or more improved properties compared with crystalline forms of the prior art and have significant values for future drug optimization and development.

Compound I

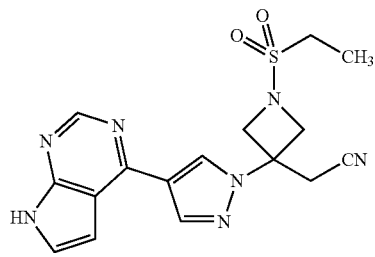

9 Claims, 9 Drawing Sheets

CRYSTAL FORM OF BARICITINIB AND PREPARATION METHOD THEREOF

CROSS-REFERENCE TO RELATED APPLICATIONS

This application is a U.S. national stage application of the PCT International Application No. PCT/CN2018/088068 filed on May 23, 2018, which claims the benefit of foreign priority of Chinese patent application No. 201710479111.9 filed on Jun. 22, 2017, the contents all of which are incorporated herein by reference.

BACKGROUND OF THE INVENTION

(1) Field of the Invention

The present disclosure relates to the field of pharmaceutical chemistry, particularly relates to novel crystalline forms of Baricitinib and processes for preparation thereof.

(2) Description of Related Art

Rheumatoid arthritis is a clinically important, chronic systemic autoimmune inflammatory disease. Most rheumatoid arthritis patients suffer a chronic course of disease that, even with currently available therapies, may result in progressive joint destruction, deformity, disability and even premature death.

The JAK (Janus kinase) is an intracellular non-receptor tyrosine kinase family. At present, four JAK family members are known: JAK 1, JAK2, JAK3 and Tyrosine kinase 2 (TYK2). The JAK-dependent cytokines participate in the pathogenic process of various inflammations and autoimmune diseases, and JAK inhibitors may be widely used for treating various inflammatory diseases.

Baricitinib is a selective JAK1 and JAK2 inhibitor developed by Incyte Corp. and later authorized to Eli Lilly. Baricitinib can be used for preparing drugs treating rheumatoid arthritis. In kinase assay, Baricitinib preferentially inhibits JAK1 and JAK2, with 100-fold selectivity over JAK3. Baricitinib was approved in Europe on Feb. 13, 2017. The chemical name of the drug is {1-(ethyl sulfonyl))-3-[4-(7H-pyrrolo[2,3-d]pyrimidine-4-yl)-1H-pyrazole-1-yl]azetidin-3-yl}acetonitrile, hereinafter referred to as Compound I.

Compound I

In the field of pharmaceutical research, different crystalline forms have different colors, melting points, solubility, dissolution performances, chemical stabilities, mechanical stabilities, etc. These characteristics can affect the quality, safety and efficacy of drug products, and lead to differences in clinical efficacy. The research and control of crystalline forms have become an important part in drug development.

WO2015166434A1 disclosed a crystalline form of Baricitinib free form (hereinafter referred to as "Form P1"). CN105693731A disclosed crystalline form A of Baricitinib free form, and crystalline form A is essentially the same as Form P1 according to the research of the inventors of the present disclosure.

It is necessary to perform comprehensive polymorph screening to get more crystalline forms with excellent properties. The crystalline form G of the present disclosure has advantages in solubility, stability, hygroscopicity, density, adhesiveness, and flowability, etc. The crystalline form G provides a better choice for the development of Baricitinib drug products, which is of great significance for improving the bioavailability and efficacy of drugs.

BRIEF SUMMARY OF THE INVENTION

The main objective of the present disclosure is to provide novel crystalline forms of Baricitinib, processes for preparation and uses thereof.

Crystalline forms of the present disclosure have advantages in at least one aspect of solubility, melting point, density, stability, dissolution, hygroscopicity, adhesiveness, flowability, bioavailability, processing performance, purification ability, and formulation production. According to the objective of the present disclosure, crystalline form G of Baricitinib is provided, hereinafter referred to as Form G.

The X-ray powder diffraction pattern of Form G shows characteristic peaks at 2theta values of 10.9°±0.2°, 16.5°±0.2° and 19.0°±0.2° using CuKα radiation.

Furthermore, the X-ray powder diffraction pattern of Form G shows one or two or three characteristic peaks at 2theta values of 14.4°±0.2°, 18.2°±0.2° and 21.8°±0.2°. Preferably, the X-ray powder diffraction pattern of Form G shows characteristic peaks at 2theta values of 14.4°±0.2°, 18.2°±0.2° and 21.8°±0.2°.

Furthermore, the X-ray powder diffraction pattern of Form G shows one or two or three characteristic peaks at 2theta values of 22.8°±0.2°, 23.8°±0.2° and 26.9°±0.2°. Preferably, the X-ray powder diffraction pattern of Form G shows characteristic peaks at 2theta values of 22.8°±0.2°, 23.8°±0.2° and 26.9°±0.2°.

Figure 1:
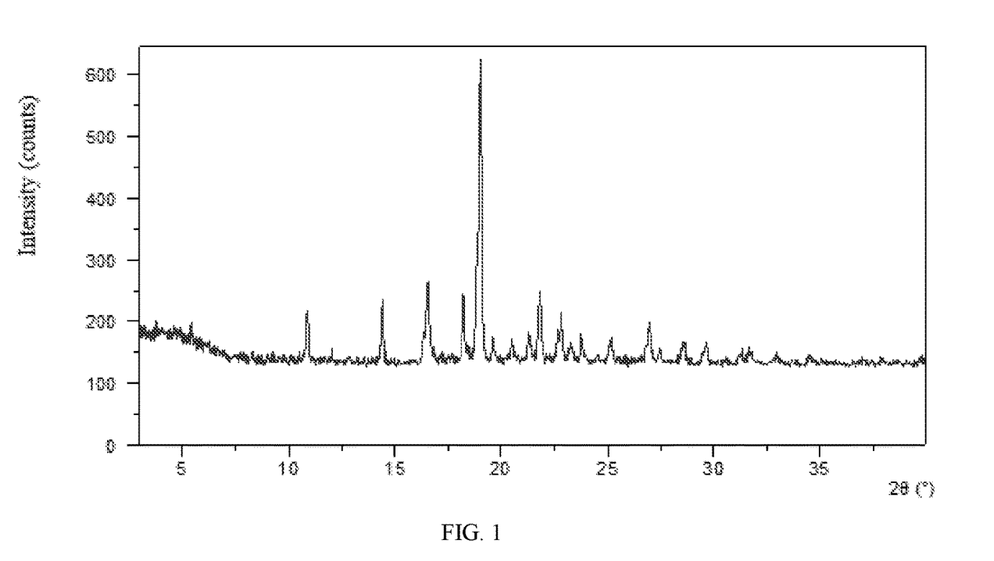
FIG. 1 shows an XRPD pattern of Form G.

Furthermore, the X-ray powder diffraction pattern of Form G shows three or four or five or six or seven or eight or nine characteristic peaks at 2theta values of 10.9°±0.2°, 14.4°±0.2°, 16.5°±0.2°, 18.2°±0.2°, 19.0°±0.2°, 21.8°±0.2°, 22.8°±0.2°, 23.8°±0.2° and 26.9°±0.2° using CuKα radiation. Without any limitation being implied, in a preferred embodiment, the X-ray powder diffraction pattern of Form G is substantially as depicted in FIG. 1.

According to another objective of the present disclosure, a process for preparing Form G is also provided. The process comprises: heating Baricitinib solid to 212-225° C., cooling to room temperature to obtain Form G.

Furthermore, said Baricitinib solid is a solvate, preferably is a chloroform solvate.

In a preferred embodiment, said process for preparing Form G comprises: heating Baricitinib chloroform solvate from room temperature to 212° C., holding for 10 minutes. The obtained sample is Form G.

According to the objective of the present disclosure, crystalline form D of Baricitinib is provided, hereinafter referred to as Form D.

The X-ray powder diffraction pattern of Form D shows characteristic peaks at 2theta values of 9.4°±0.2°, 16.6°±0.2° and 19.0°±0.2° using CuKα radiation.

Furthermore, the X-ray powder diffraction pattern of Form D shows one or more characteristic peaks at 2theta values of 17.5°±0.2°, 25.5°±0.2° and 26.1°±0.2°. Preferably, the X-ray powder diffraction pattern of Form D shows characteristic peaks at 2theta values of 17.5°±0.2°, 25.5°±0.2° and 26.1°±0.2°.

Furthermore, the X-ray powder diffraction pattern of Form D shows one or more characteristic peaks at 2theta values of 12.4°±0.2°, 19.9°±0.2° and 21.3°±0.2°. Preferably, the X-ray powder diffraction pattern of Form D shows characteristic peaks at 2theta values of 12.4°±0.2°, 19.9°±0.2° and 21.3°±0.2°.

In a preferred embodiment, the X-ray powder diffraction pattern of Form D shows characteristic peaks at 2theta values of 9.4°±0.2°, 12.4°±0.2°, 16.6°±0.2°, 17.5°±0.2°, 19.0°±0.2°, 19.9°±0.2°, 21.3°±0.2°, 25.5°±0.2° and 26.1°±0.2° using CuKα radiation.

Figure 2:
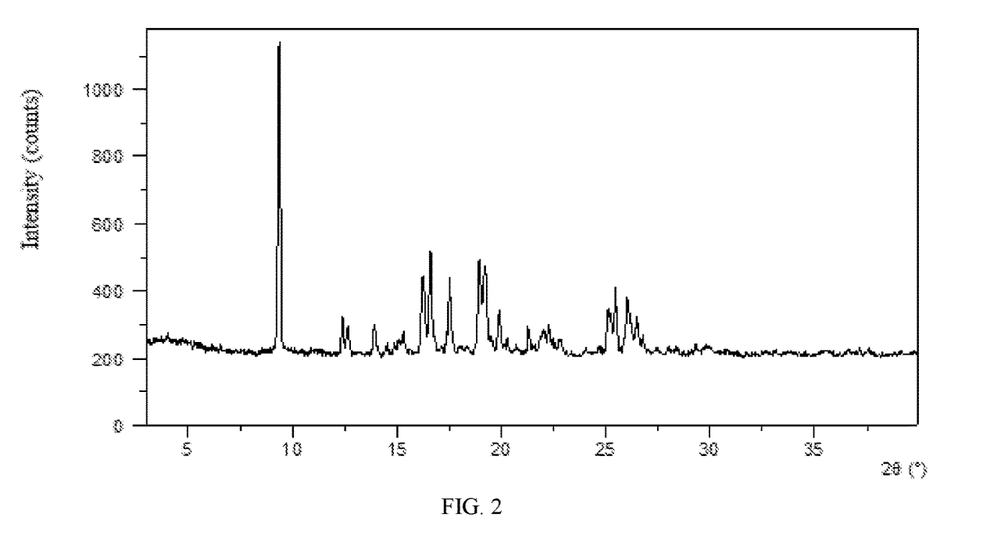
FIG. 2 shows an XRPD pattern of Form D.

Without any limitation being implied, in a preferred embodiment, the X-ray powder diffraction pattern of Form D is substantially as depicted in FIG. 2.

Without any limitation being implied, in a preferred embodiment, Form D is a 1, 4-dioxane solvate.

According to another objective of the present disclosure, a process for preparing Form D is also provided. The process comprises:

Adding Baricitinib solid into a reactor, adding 1,4-dioxane to get a suspension, stirring at room temperature for 1-7 days, and centrifuging to obtain Form D. Said stirring time is preferably one day.

According to the objective of the present disclosure, crystalline form E of Baricitinib is provided, hereinafter referred to as Form E.

The X-ray powder diffraction pattern of Form E shows characteristic peaks at 2theta values of 9.7°±0.2°, 18.1°±0.2° and 19.1°±0.2° using CuKα radiation.

Furthermore, the X-ray powder diffraction pattern of Form E shows one or more characteristic peaks at 2theta values of 21.3°±0.2°, 24.6°±0.2° and 27.7°±0.2°. Preferably, the X-ray powder diffraction pattern of Form E shows characteristic peaks at 2theta values of 21.3°±0.2°, 24.6°±0.2° and 27.7°±0.2°.

Furthermore, the X-ray powder diffraction pattern of Form E shows one or more characteristic peaks at 2theta values of 21.5°±0.2°, 22.5°±0.2° and 26.6°±0.2°. Preferably, the X-ray powder diffraction pattern of Form E shows characteristic peaks at 2theta values of 21.5°±0.2°, 22.5°±0.2° and 26.6°±0.2°.

In a preferred embodiment, the X-ray powder diffraction pattern of Form E shows characteristic peaks at 2theta values of 9.7°±0.2°, 18.1°±0.2°, 19.1°±0.2°, 21.3°±0.2°, 21.5°±0.2°, 22.5°±0.2°, 24.6°±0.2°, 26.6°±0.2° and 27.7°±0.2° using CuKα radiation.

Figure 5:
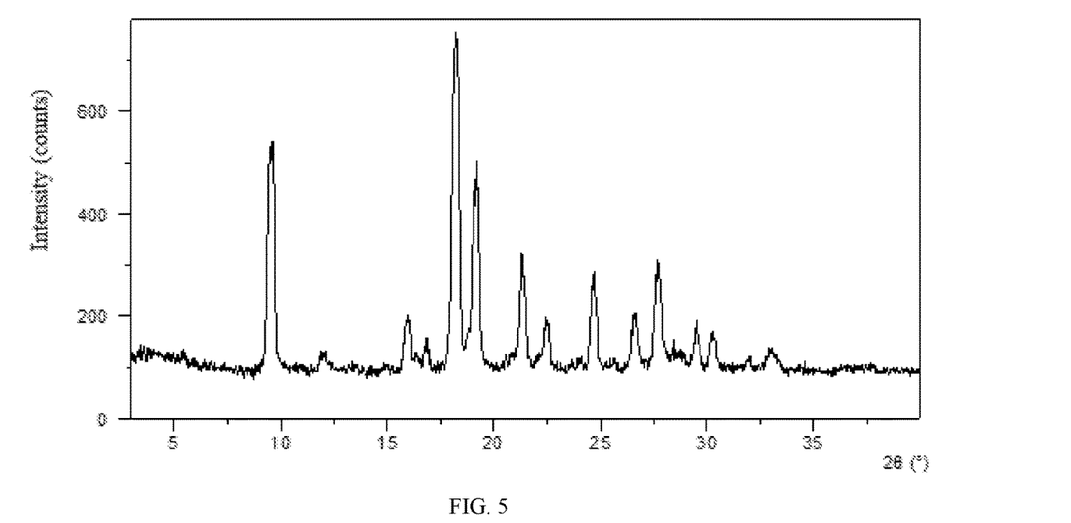
FIG. 5 shows an XRPD pattern of Form E.

Without any limitation being implied, in a preferred embodiment, the X-ray powder diffraction pattern of Form E is substantially as depicted in FIG. 5.

Without any limitation being implied, in a preferred embodiment, Form E is a chloroform solvate.

According to another objective of the present disclosure, a process for preparing Form E is also provided. The process comprises:

Adding Baricitinib solid into a reactor, adding chloroform to get a suspension, stirring at room temperature for 0.5-7 days, and evaporating to obtain Form E. Said stirring time is preferably one day.

According to the objective of the present disclosure, crystalline form F of Baricitinib is provided, hereinafter referred to as Form F.

The X-ray powder diffraction pattern of Form F shows characteristic peaks at 2theta values of 9.0°±0.2°, 16.9°±0.2° and 18.1°±0.2° using CuKα radiation.

Furthermore, the X-ray powder diffraction pattern of Form F shows one or more characteristic peaks at 2theta values of 17.3°±0.2°, 20.0°±0.2° and 26.3°±0.2°. Preferably, the X-ray powder diffraction pattern of Form F shows characteristic peaks at 2theta values of 17.3°±0.2°, 20.0°±0.2° and 26.3°±0.2°.

Furthermore, the X-ray powder diffraction pattern of Form F shows one or more characteristic peaks at 2theta values of 15.5°±0.2°, 22.1°±0.2° and 23.6°±0.2°. Preferably, the X-ray powder diffraction pattern of Form F shows characteristic peaks at 2theta values of 15.5°±0.2°, 22.1°±0.2° and 23.6°±0.2°.

In a preferred embodiment, the X-ray powder diffraction pattern of Form F shows characteristic peaks at 2theta values of 9.0°±0.2°, 15.5°±0.2°, 16.9°±0.2°, 17.3°±0.2°, 18.1°±0.2°, 20.0°±0.2°, 22.1°±0.2°, 23.6°±0.2° and 26.3°±0.2° using CuKα radiation.

Figure 8:
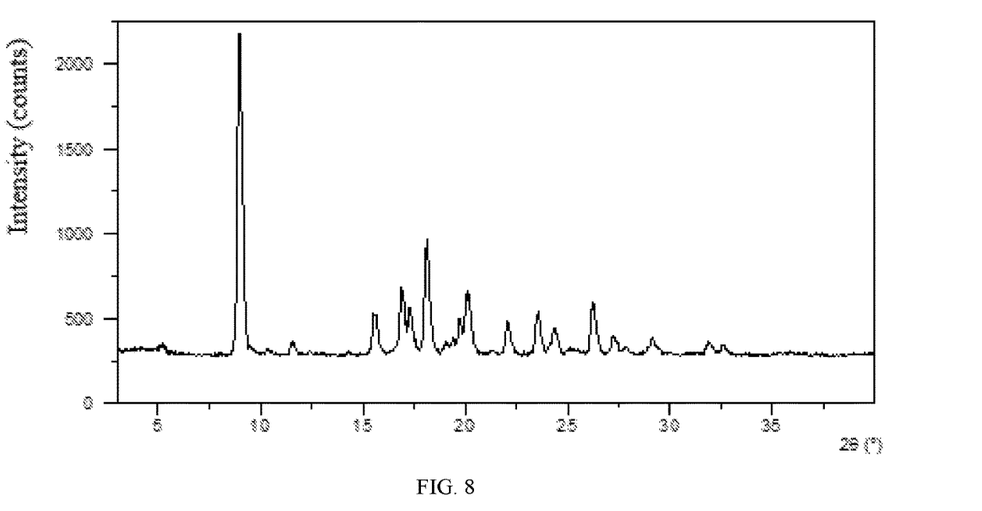
FIG. 8 shows an XRPD pattern of Form F.

Without any limitation being implied, in a preferred embodiment, the X-ray powder diffraction pattern of Form F is substantially as depicted in FIG. 8.

Without any limitation being implied, in a preferred embodiment, Form F is a methyl tert butyl ether solvate.

According to another objective of the present disclosure, a process for preparing Form F is also provided. The process comprises:

Adding Baricitinib Form E into a reactor, adding methyl tert butyl ether to get a suspension, stirring at room temperature for at least 1 hour, and centrifuging to obtain Form F.

In the process for preparing crystalline forms of the present disclosure:

Said "room temperature" is not a specific value, and refers to 10-30° C.

Said "stirring" is accomplished by using a conventional method in the field such as magnetic stirring or mechanical stirring and the stirring speed is 50 to 1800 r/min, preferably the speed is 300 to 900 r/min.

Said "centrifuging" is as follows: the sample to be separated is placed into the centrifuge tube, and then centrifuged at a rate of 10000 r/min until all the solid sinks to the bottom of the tube.

Said "evaporating" is accomplished by using a conventional method in the field, for example, slow evaporation is accomplished in a container covered by sealing film with pinholes, and rapid evaporation is accomplished in an open container.

According to the present disclosure, Baricitinib and/or its salt used as a raw material is solid (crystalline and amorphous), semisolid, wax or oil. Preferably, said Baricitinib and/or its salt used as a raw material is a solid.

In the present disclosure, "crystal" or "crystalline form" refers to the crystal or the crystalline form being identified by the X-ray diffraction pattern shown herein. Those skilled in the art are able to understand that physicochemical properties discussed herein can be characterized. The experimental errors depend on the instrument conditions, the sampling processes and the purity of samples. In particular, those skilled in the art generally know that the X-ray diffraction pattern typically varies with the experimental conditions. It is necessary to point out that, the relative intensity of the diffraction peaks in the X-ray diffraction pattern may also vary with the experimental conditions; therefore, the order of the diffraction peak intensities cannot be regarded as the sole or decisive factor. In fact, the relative intensity of the diffraction peaks in the X-ray powder diffraction pattern is related to the preferred orientation of the crystals, and the diffraction peak intensities shown herein are illustrative and identical diffraction peak intensities are not required. In addition, the experimental error of the diffraction peak position is usually 5% or less, and the error of these positions should also be taken into account. An error of ±0.2° is usually allowed. In addition, due to experimental factors such as sample thickness, the overall offset of the diffraction peak is caused, and a certain offset is usually allowed. Thus, it will be understood by those skilled in the art that a crystalline form of the present disclosure is not necessarily to have the exactly same X-ray diffraction pattern of the example shown herein. As used herein, "the same XRPD pattern" does not mean absolutely the same, the same peak positions may differ by ±0.2° and the peak intensity allows for some variability. Any crystalline forms whose X-ray diffraction patterns have the same or similar characteristic peaks should be within the scope of the present disclosure. Those skilled in the art can compare the patterns shown in the present disclosure with that of an unknown crystalline form in order to identify whether these two groups of patterns reflect the same or different crystalline forms.

It should be noted that the number and the number range should not be understood as the number or number range themselves only. It should be understood by those skilled in the art that the specific number can be shifted at specific technical environment without departing from the spirit and principle of the present disclosure. In the present disclosure, the shift ranges expected by those of skilled in the art is represented by the term "about".

In addition, the present disclosure provided a pharmaceutical composition, said pharmaceutical composition comprises a therapeutically effective amount of Form G and pharmaceutically acceptable carriers, diluents or excipients.

Furthermore, Form G can be used for preparing drugs inhibiting JAK.

Furthermore, Form G can be used for preparing drugs treating autoimmune diseases.

Furthermore, Form G can be used for preparing drugs treating rheumatoid arthritis.

Compared with prior art (Form P1 and Form A), Form G of the present disclosure has the following advantages:

(1) Compared with prior art, Form G has higher solubility. Compared with the prior art, solubility of Form G of the present disclosure in the biological media has been significantly improved. Particularly in FaSSIF, the solubility of Form G is 7 times higher than that of the prior art. In FeSSIF, the solubility of Form G is 6 times higher than that of the prior art. In water, the solubility of Form G is 7 times higher than that of the prior art. In SGF, the solubility of Form G is 1.5 times higher than that of prior art. A prominent increase in solubility of Form G is conducive to increase the bioavailability of drugs, thereby increasing the possibility of a successful drug product and also increasing the drug efficacy. Drug dose reduction without affecting efficacy is possible due to higher solubility, thereby reducing the drug's side effects and improving drug safety.

(2) Compared with prior art, Form G of the present disclosure has lower hygroscopicity. The test results show that the hygroscopicity of Form G of the present disclosure is less than that of the prior art at any relative humidity (RH) of 0-95% RH. The hygroscopicity of the prior art is 2-7 times higher than that of Form G. Crystalline forms with low hygroscopicity require no special drying conditions, and simplify the preparation and post-treatment of drugs. It is also easy to industrialize. In addition, crystalline forms with low hygroscopicity are conducive to the long-term storage of drugs. Crystalline forms with low hygroscopicity don't require special storage conditions, which reduces the cost of materiel storage and quality control, and has strong economic values.

(3) Compared with prior art, Form G of the present disclosure has higher density. Test results indicate that the bulk density and tapped density of Form G are remarkably higher than that of the prior art. Particularly, bulk density of Form G is 4 times higher than that of the prior art, and tapped density of Form G is 3 times higher than that of the prior art. Higher density of Form G is beneficial to large scale production. Higher density of Form G can also reduce dust, occupational hazard and security risks, which ensures production safety.

(4) Compared with prior art, Form G of the present disclosure has better flowability. Flowability evaluation results indicate that the flowability of Form G is good, and the flowability of the prior art form is very poor. From the perspective of production efficiency and cost, better flowability can effectively improve the production speed and efficiency of tableting and filling, and increase the manufacturing efficiency. There is no need to use some expensive special excipients to improve the flowability, thus reduces the excipient cost. In addition, better flowability can improve the feasibility of direct tableting and filling, which greatly simplifies the production process and reduces the cost. From the perspective of product quality, better flowability of Form G ensures the blend uniformity and content uniformity of the drug product, reduces the weight variation in the drug product and improves product quality.

(5) Compared with prior art, Form G of the present disclosure shows superior adhesiveness. Adhesiveness evaluation results indicate that adhesion quantity of Form G is remarkably lower than that of the prior art. The adhesion quantity of prior art is more than 3 times higher than that of Form G. From the perspective of product quality, superior adhesiveness of Form G can effectively reduce adhesion to roller and tooling during dry-granulation and tableting, which is also beneficial to improve product appearance and weight variation. In addition, superior adhesiveness of Form G can reduce the agglomeration of drug substance, and reduce adhesion between materials and instruments, which is beneficial to the dispersion of drug substance and drug substances with other excipients, and improves the blend uniformity and content uniformity of drug product.

(6) Form G of the present disclosure has good physical stability. Form G is stable for at least 6 months under the long term stability conditions (25° C./60% RH) of Pharmacopoeia of the People's Republic of China, and for at least 6 months when stored under the accelerated stability conditions (40° C./75% RH) of Pharmacopoeia of the People's Republic of China, and for at least 1 week when stored under more harsh high temperature and humidity conditions (60° C./75% RH and 80° C.). It can be proved from this that From G has very good physical stability. As the most critical active ingredient in drug, it is very important that the crystalline active pharmaceutical ingredients have good physical and chemical stability. Good physical stability ensures that the active pharmaceutical ingredients cannot easily change into other crystalline forms during storage and preparation process, so as to ensure the consistent and controllable quality of samples. The good chemical stability of the crystalline forms helps the purity hold basically unchanged during storage, which is of great significance to ensure the efficacy and safety of drugs and prevent the occurrence of adverse drug effects. In addition, the stable crystalline form is more controllable in the crystallization process, and less prone to impurities and mixed crystals, which is conducive to industrial production.

DESCRIPTION OF PREFERRED EMBODIMENTS

The present disclosure will be further explained by the specific embodiments. These specific embodiments are not to restrict the scope of the present disclosure. The skilled in the art can make improvements to the preparation process and the instruments within the scope of the claims, and those improvements should be considered as within the scope of the present disclosure. Therefore, the scope of the present disclosure should be defined by the claims.

In the following examples, the test method is generally implemented according to a conventional condition or a condition that recommended by the manufacturer.

The abbreviations used in the present disclosure are explained as follows:
XRPD: X-ray Powder Diffraction
DSC: Differential Scanning calorimetry
TGA: Thermo Gravimetric Analysis
$^1$H NMR: Proton Nuclear Magnetic Resonance X-ray powder diffraction patterns in the present disclosure were acquired by a Panalytical Empyrean X-ray powder diffractometer. The parameters of the X-ray powder diffraction method of the present disclosure were as follows:
X-ray Reflection: Cu, Kα
Kα1 (Å): 1.540598; Kα2 (Å): 1.544426
Kα2/Kα1 intensity ratio: 0.50
Voltage: 45 (kV)
Current: 40 (mA)
Scan range: from 3.0 degree to 40.0 degree Differential scanning calorimetry (DSC) data in the present disclosure were acquired by a TA Q2000. The parameters of the DSC method of the present disclosure were as follows:
Heating rate: 10° C./min
Purge gas: nitrogen Thermo gravimetric analysis (TGA) data in the present disclosure were acquired by a TA Q5000. The parameters of the TGA method of the present disclosure were as follows:
Heating rate: 10° C./min
Purge gas: nitrogen Proton nuclear magnetic resonance spectrum data ($^1$H NMR) were collected from a Bruker Avance II DMX 400M HZ NMR spectrometer. 1-5 mg of sample was weighed, and dissolved in 0.5 mL of deuterated dimethyl sulfoxide to obtain a solution with a concentration of 2-10 mg/mL.

Figure 11:
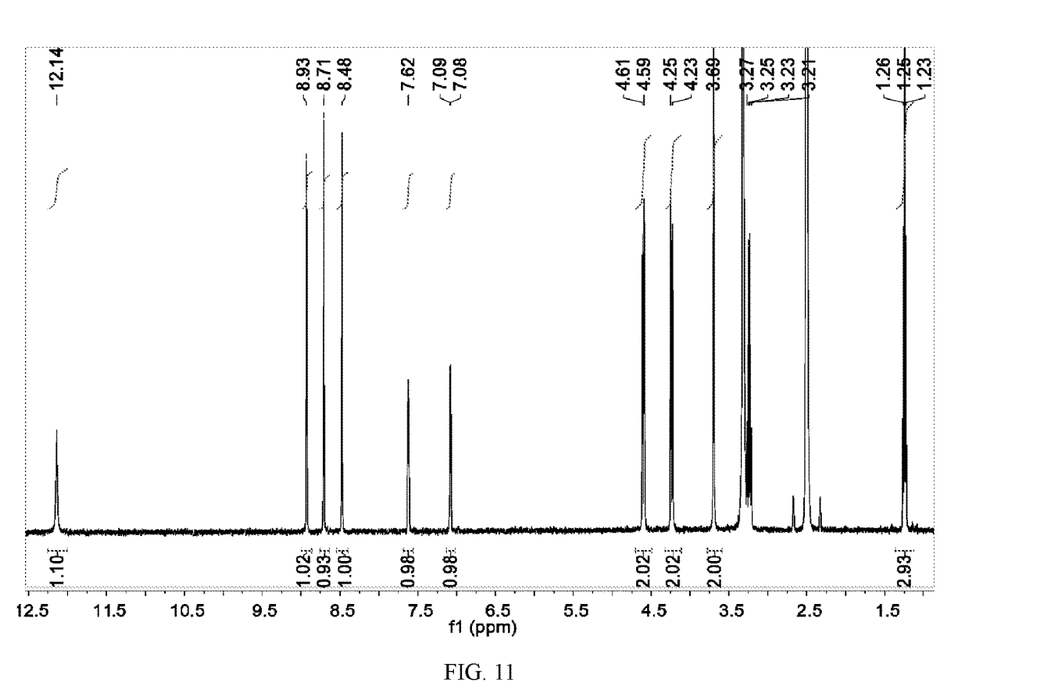
FIG. 11 shows a $^1$H NMR spectrum of Form G.
Figure 15:
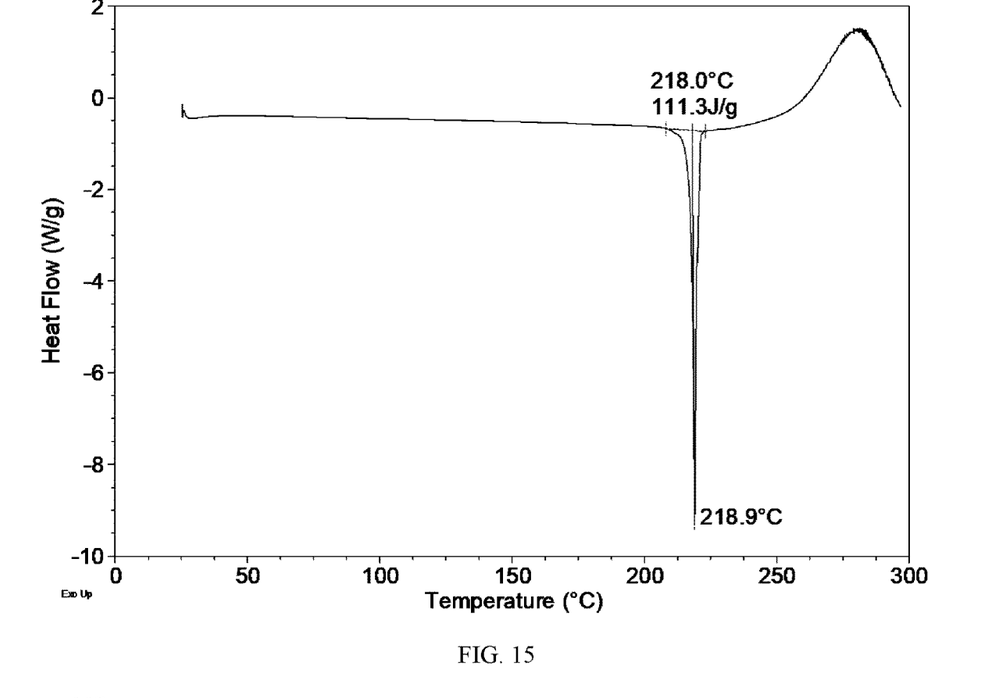
FIG. 15 shows a DSC curve of Form G.
Figure 16:
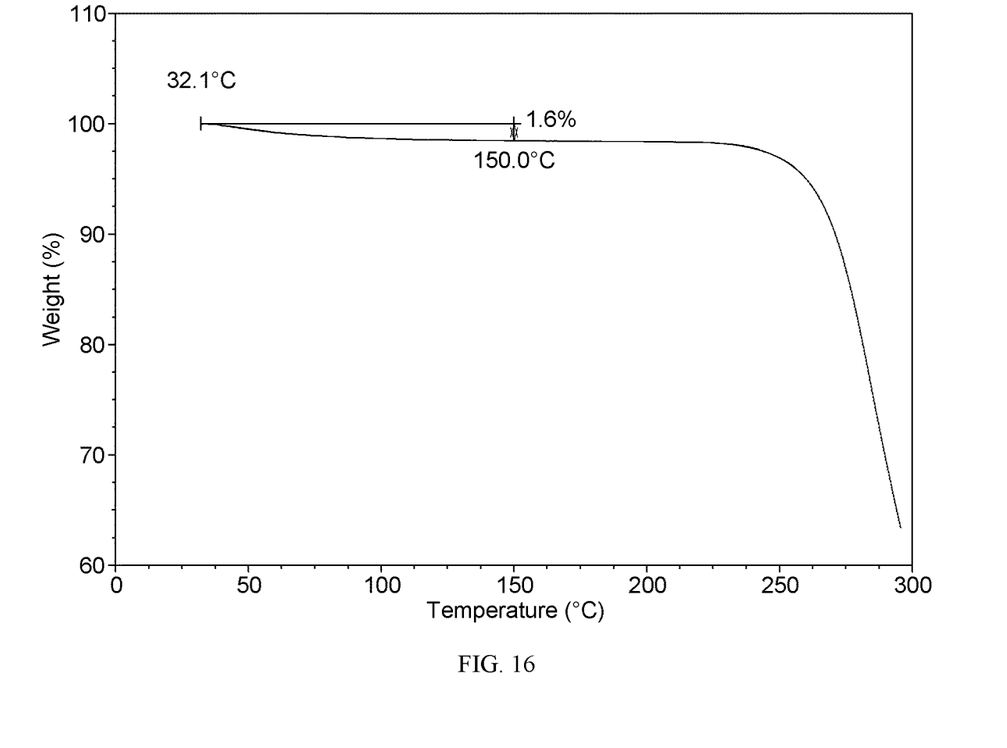
FIG. 16 shows a TGA curve of Form G.

Example 1 Preparation of Form G of Baricitinib 2 mg of Baricitinib Form E was weighed and heated by a DSC with the speed of 10° C./min from room temperature to 212° C. The sample was kept at 212° C. for 10 minutes. The obtained sample was confirmed to be Form G by XRPD. The XRPD pattern is substantially as depicted in FIG. 1, and the XRPD data are listed in Table 1. The DSC curve of Form G is substantially as depicted in FIG. 15, which shows an endothermic peak at around 218° C. (onset temperature). The TGA curve of Form G is substantially as depicted in FIG. 16, which shows about 1.6% weight loss when heated to 150° C. The $^1$H NMR spectrum of Form G is substantially as depicted in FIG. 11, and the corresponding data are: δ H (400 MHz, DMSO) 12.14 (1H, s), 8.93 (1H, s), 8.71 (1H, s), 8.48 (1H, s), 7.62 (1H, s), 7.08 (1H, d, J 3.4), 4.60 (2H, d, J 9.1), 4.24 (2H, d, J 9.1), 3.69 (2H, s), 3.24 (2H, q, J 7.4), 1.25 (3H, t, J 7.3).

TABLE 1

| 2θ | d spacing | Intensity % |
|---|---|---|
| 10.89 | 8.12 | 13.97 |
| 14.41 | 6.15 | 20.76 |
| 16.53 | 5.36 | 26.89 |
| 18.23 | 4.87 | 22.48 |
| 19.03 | 4.66 | 100.00 |
| 19.65 | 4.52 | 6.95 |
| 20.52 | 4.33 | 6.78 |
| 21.29 | 4.17 | 9.90 |
| 21.78 | 4.08 | 20.51 |
| 22.82 | 3.90 | 14.85 |
| 23.30 | 3.82 | 5.28 |
| 23.77 | 3.74 | 8.43 |
| 25.16 | 3.54 | 7.78 |
| 26.94 | 3.31 | 13.34 |
| 28.56 | 3.13 | 6.77 |
| 29.62 | 3.02 | 6.32 |
| 31.66 | 2.83 | 3.73 |
| 32.96 | 2.72 | 2.76 |
| 34.47 | 2.60 | 2.22 |

Figure 3:
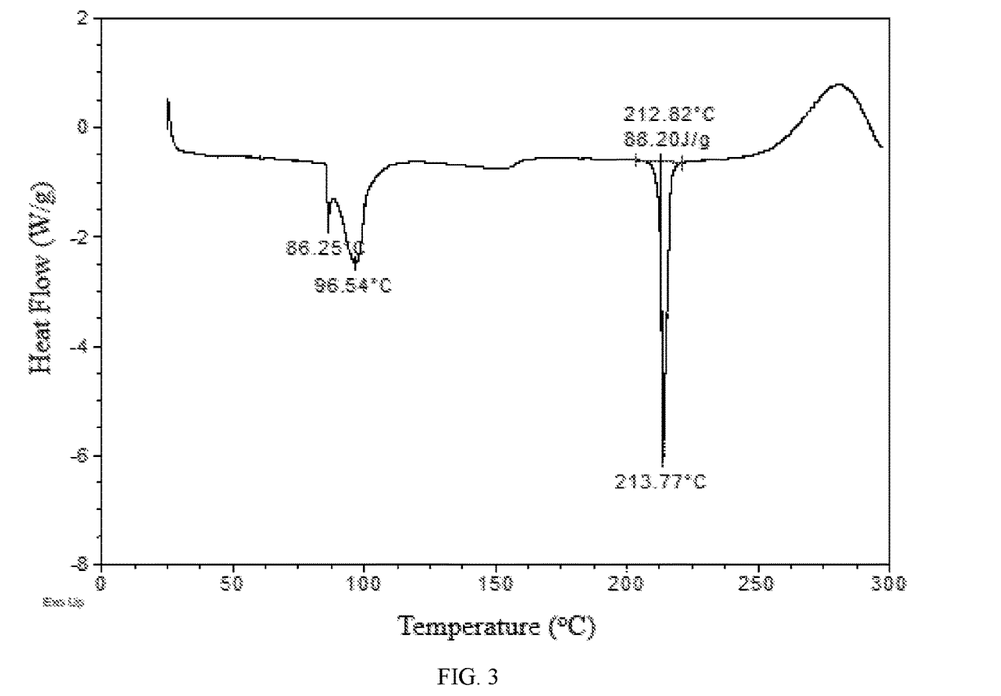
FIG. 3 shows a DSC curve of Form D.
Figure 4:
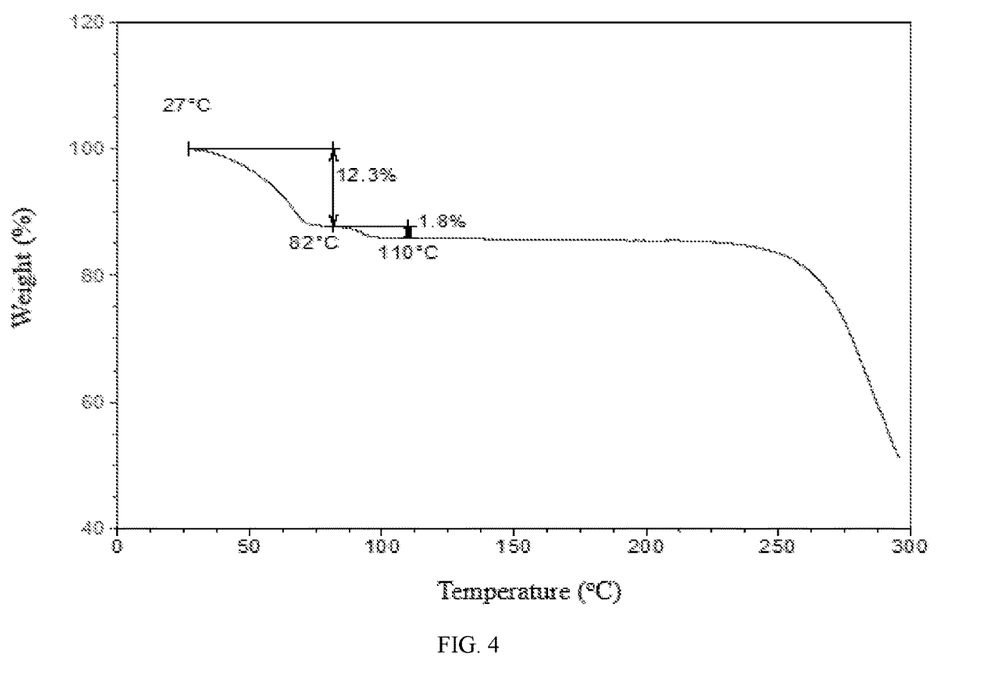
FIG. 4 shows a TGA curve of Form D.

Example 2 Preparation of Form D of Baricitinib 59.1 mg of Baricitinib crystalline form (WO2015166434A1) was weighed into a 1.5-mL glass vial followed by adding 1 mL of 1,4-dioxane to get a suspension. The suspension was stirred at room temperature for one day, then centrifuged to obtain solid. The obtained sample was confirmed to be Form D by XRPD. The XRPD pattern is substantially as depicted in FIG. 2, and the XRPD data are listed in Table 2. The DSC curve of Form D is substantially as depicted in FIG. 3, which shows an endothermic peak at around 86° C. (onset temperature) corresponding to the loss of solvent. The TGA curve of Form D is substantially as depicted in FIG. 4, which shows about 14.1% weight loss when heated to 110° C.

TABLE 2

| 2θ | d spacing | Intensity % |
|---|---|---|
| 9.39 | 9.42 | 100.00 |
| 12.42 | 7.13 | 11.80 |
| 12.66 | 6.99 | 8.83 |
| 13.90 | 6.37 | 7.98 |
| 14.53 | 6.10 | 3.87 |
| 15.33 | 5.78 | 7.45 |
| 16.22 | 5.46 | 23.78 |
| 16.60 | 5.34 | 33.61 |
| 17.52 | 5.06 | 23.64 |
| 18.00 | 4.93 | 2.51 |
| 18.97 | 4.68 | 30.35 |
| 19.24 | 4.61 | 27.37 |
| 19.88 | 4.47 | 11.66 |
| 20.30 | 4.37 | 4.17 |
| 21.28 | 4.17 | 9.29 |
| 21.96 | 4.05 | 6.82 |
| 22.29 | 3.99 | 8.63 |
| 22.82 | 3.90 | 4.88 |
| 24.07 | 3.70 | 1.62 |
| 25.12 | 3.55 | 14.52 |
| 25.50 | 3.49 | 17.43 |
| 26.05 | 3.42 | 18.22 |
| 26.50 | 3.36 | 10.54 |
| 26.78 | 3.33 | 6.72 |
| 28.23 | 3.16 | 1.16 |
| 29.89 | 2.99 | 2.37 |
| 35.54 | 2.53 | 1.37 |
| 36.62 | 2.45 | 1.49 |
| 37.58 | 2.39 | 1.75 |

Figure 6:
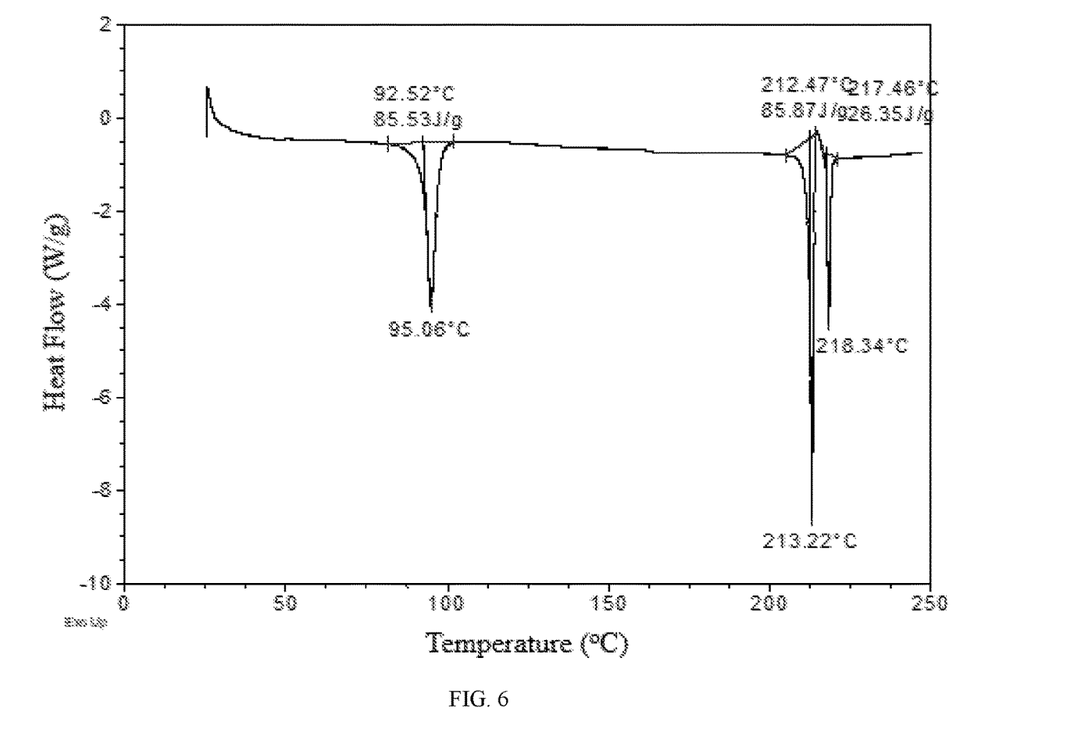
FIG. 6 shows a DSC curve of Form E.
Figure 7:
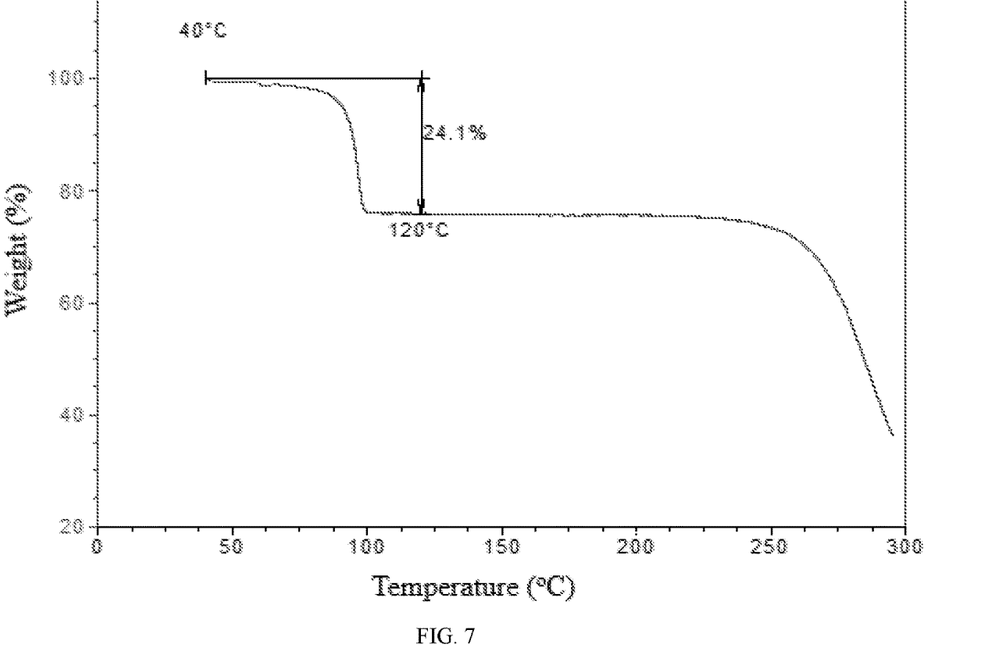
FIG. 7 shows a TGA curve of Form E.

Example 3 Preparation of Form E of Baricitinib 106.3 mg of Baricitinib was weighed and dissolved in 1.0 mL of acetic acid, and the solution was evaporated at room temperature to obtain solid. 10.0 mg of the obtained solid was weighed to a 1.5-mL glass vial, and then 0.5 mL of chloroform was added to get a suspension. The suspension was stirred at room temperature for one day, and chloroform was evaporated to obtain solid. The obtained solid sample was confirmed to be Form E by XRPD. The XRPD pattern is substantially as depicted in FIG. 5, and the XRPD data are listed in Table 3. The DSC curve of Form E is substantially as depicted in FIG. 6, which shows an endothermic peak at around 93° C. (onset temperature) corresponding to the loss of solvent. The TGA curve of Form E is substantially as depicted in FIG. 7, which shows about 24.1% weight loss when heated to 120° C.

TABLE 3

| 2θ | d spacing | Intensity % |
|---|---|---|
| 9.44 | 9.37 | 64.72 |
| 9.69 | 9.13 | 66.67 |
| 11.95 | 7.41 | 5.01 |
| 16.06 | 5.52 | 14.69 |
| 16.85 | 5.26 | 9.58 |
| 18.10 | 4.90 | 100.00 |
| 18.33 | 4.84 | 91.75 |
| 19.06 | 4.66 | 58.91 |
| 19.27 | 4.61 | 52.75 |
| 21.31 | 4.17 | 39.65 |
| 21.45 | 4.14 | 25.91 |
| 22.54 | 3.94 | 15.53 |
| 24.60 | 3.62 | 28.66 |
| 26.58 | 3.35 | 18.93 |
| 27.75 | 3.22 | 31.84 |
| 29.49 | 3.03 | 15.41 |
| 30.19 | 2.96 | 10.78 |

TABLE 3-continued

| 2θ | d spacing | Intensity % |
|---|---|---|
| 31.93 | 2.80 | 3.64 |
| 32.96 | 2.72 | 6.37 |

Figure 9:
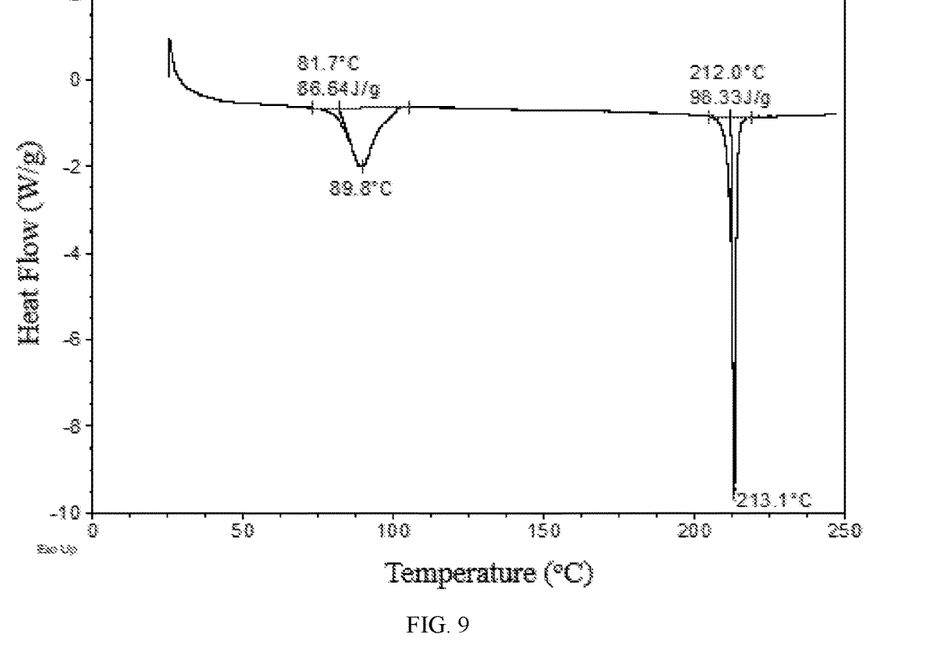
FIG. 9 shows a DSC curve of Form F.
Figure 10:
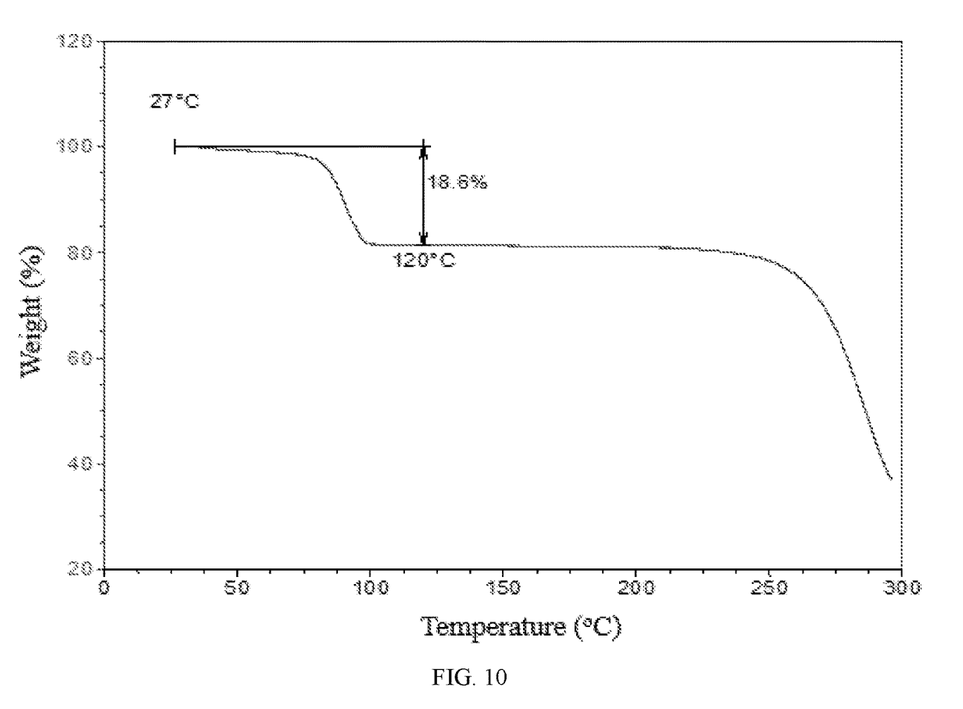
FIG. 10 shows a TGA curve of Form F.

Example 4 Preparation of Form F of Baricitinib 10.7 mg of Baricitinib Form E was weighed into a 1.5-mL glass vial, and then 0.5 mL of methyl tert butyl ether was added to get a suspension. The suspension was stirred at room temperature for one hour, then centrifuged to obtain solid, which was confirmed to be Form F by XRPD. The XRPD pattern is substantially as depicted in FIG. 8, and the XRPD data are listed in Table 4. The DSC curve of Form F is substantially as depicted in FIG. 9, which shows an endothermic peak at around 82° C. (onset temperature) corresponding to the loss of solvent. The TGA curve of Form F is substantially as depicted in FIG. 10, which shows about 18.6% weight loss when heated to 120° C.

TABLE 4

| 2θ | d spacing | Intensity % |
|---|---|---|
| 4.18 | 21.12 | 1.00 |
| 5.15 | 17.16 | 2.34 |
| 8.98 | 9.85 | 100.00 |
| 10.36 | 8.54 | 1.44 |
| 11.53 | 7.67 | 3.70 |
| 12.41 | 7.14 | 1.21 |
| 14.33 | 6.18 | 0.89 |
| 15.52 | 5.71 | 13.39 |
| 16.87 | 5.26 | 19.81 |
| 17.25 | 5.14 | 15.16 |
| 18.10 | 4.90 | 34.85 |
| 19.42 | 4.57 | 5.30 |
| 19.74 | 4.50 | 10.16 |
| 20.04 | 4.43 | 18.27 |
| 21.34 | 4.16 | 1.55 |
| 22.07 | 4.03 | 10.76 |
| 23.45 | 3.79 | 10.81 |
| 23.61 | 3.77 | 12.61 |
| 24.37 | 3.65 | 8.83 |
| 25.10 | 3.55 | 1.85 |
| 26.15 | 3.41 | 14.20 |
| 26.25 | 3.39 | 15.18 |
| 27.16 | 3.28 | 5.38 |
| 27.83 | 3.21 | 2.45 |
| 29.10 | 3.07 | 4.85 |
| 31.90 | 2.81 | 3.44 |
| 32.60 | 2.75 | 2.76 |
| 35.30 | 2.54 | 0.51 |

Example 5 Kinetic Solubility of Form G

Simulated gastrointestinal fluids such as SGF (Simulated gastric fluids), FaSSIF (Fasted state simulated intestinal fluids) and FeSSIF (Fed state simulated intestinal fluids) are biorelevant media. Solubility in such media is close to that in human environment, because these media can better reflect the effects of gastrointestinal environment on drug release. 20 mg of Form G and 20 mg of crystalline form of the prior art were suspended into 1.5 mL of SGF, 1.5 mL of FaSSIF, 1.5 mL of FaSSIF and 1.5 mL of water to get saturated solutions. After equilibrated for 1 h, 4 h and 24 h, concentrations of the saturated solutions were measured by HPLC (mg/mL). The results are listed in Table 5.

TABLE 5

| | Crystalline form of the prior art | | | Form G | | |
|---|---|---|---|---|---|---|
| Media | 1 h (mg/mL) | 4 h (mg/mL) | 24 h (mg/mL) | 1 h (mg/mL) | 4 h (mg/mL) | 24 h (mg/mL) |
| SGF | 1.900 | 1.900 | 1.900 | 2.600 | 2.700 | 2.800 |
| FaSSIF | 0.016 | 0.018 | 0.018 | 0.081 | 0.100 | 0.140 |
| FeSSIF | 0.035 | 0.031 | 0.033 | 0.130 | 0.170 | 0.220 |
| Water | 0.0089 | 0.012 | 0.013 | 0.052 | 0.066 | 0.096 |

The results in Table 5 show that the solubility of Form G is much higher than that of the crystalline form of the prior art at each sampling point in SGF, FaSSIF, FeSSIF and water. Particularly, the solubility of Form G is 7 times higher than that of the crystalline form of the prior art, which can greatly increase the bioavailability.

Example 6 Stability of Form G

Figure 17:
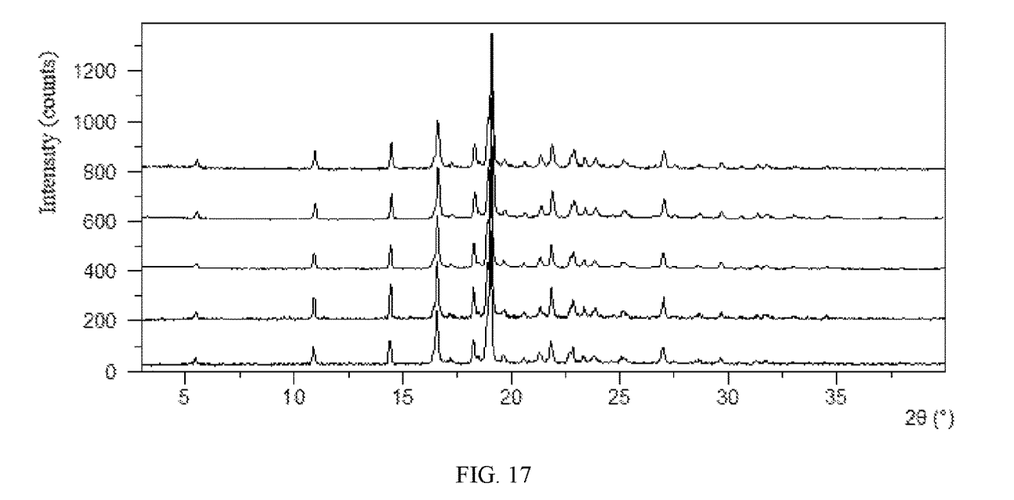
FIG. 17 shows an XRPD pattern overlay of Form G from stability study (from top to bottom: XRPD pattern of initial Form G, Form G after storing at 25° C./60% RH for 6 months, Form G after storing at 40° C./75% RH for 6 months, Form G after storing at 60° C./75% RH for 1 week, and Form G after storing at 80° C. for 1 week).

Approximately 5 mg of solid samples of Baricitinib Form G were stored under different conditions of 25° C./60% RH, 40° C./75% RH, 60° C./75% RH and 80° C. Crystalline forms were checked by XRPD. The results are shown in Table 6, and the XRPD overlay is shown in FIG. 17.

TABLE 6

| Initial crystalline form | Conditions | Time | Crystalline form |
|---|---|---|---|
| Form G | 25° C./60% RH | 6 months | Form G |
| | 40° C./75% RH | 6 months | Form G |
| | 60° C./75% RH | 1 week | Form G |
| | 80° C. | 1 week | Form G |

The results show that Form G holds stable for at least 6 months at 25° C./60% RH and 40° C./75% RH. Form G holds stable for at least 1 week at 60° C./75% RH and 80° C. It can be seen that Form G has good stability under both long-term and accelerated conditions.

Example 7 Hygroscopicity of Form G

Dynamic vapor sorption (DVS) was applied to test hygroscopicity of Form G and the crystalline form of the prior art with about 10 mg of samples. The weight gains at each relative humidity were recorded in a cycle of 0-95%-0 RH.

TABLE 7

| | Weight gain % | |
|---|---|---|
| Relative humidity | Crystalline form of the prior art | Form G |
| 0 | 0 | 0 |
| 10% | 0.07 | 0.01 |
| 20% | 0.11 | 0.03 |
| 30% | 0.15 | 0.04 |
| 40% | 0.19 | 0.06 |
| 50% | 0.24 | 0.07 |
| 60% | 0.30 | 0.10 |
| 70% | 0.36 | 0.15 |
| 80% | 0.44 | 0.21 |
| 90% | 0.59 | 0.27 |
| 95% | 0.78 | 0.34 |

Figure 12:
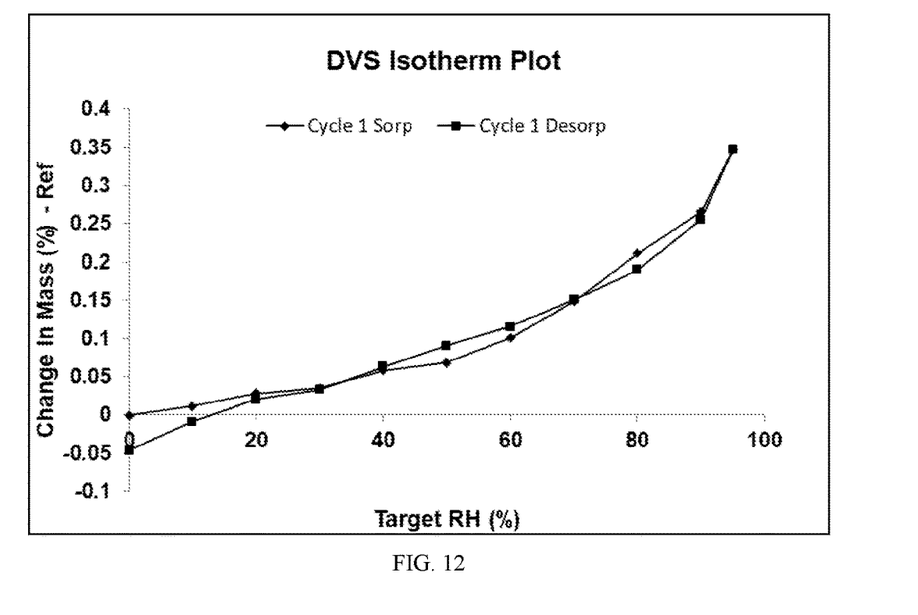
FIG. 12 shows a DVS plot of Form G.
Figure 13:
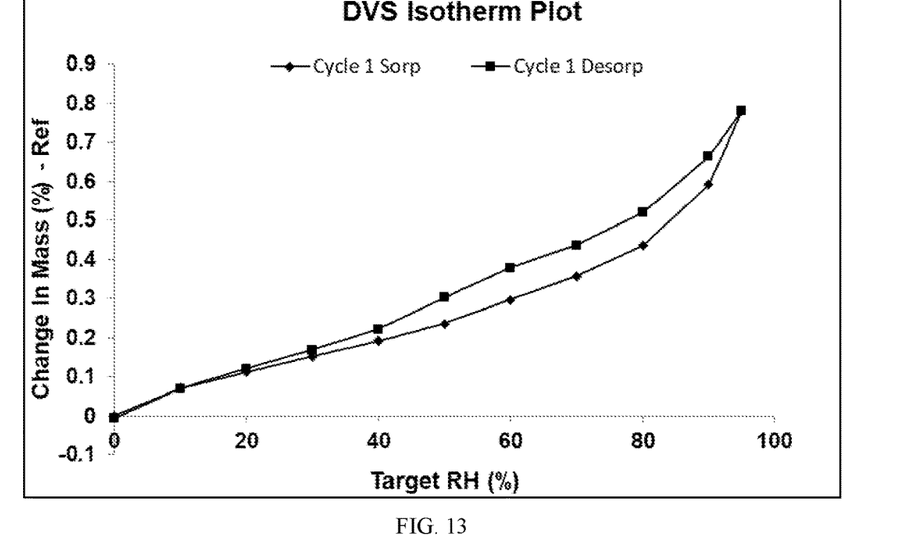
FIG. 13 shows a DVS plot of the crystalline form in WO2015166434A1.
Figure 14:
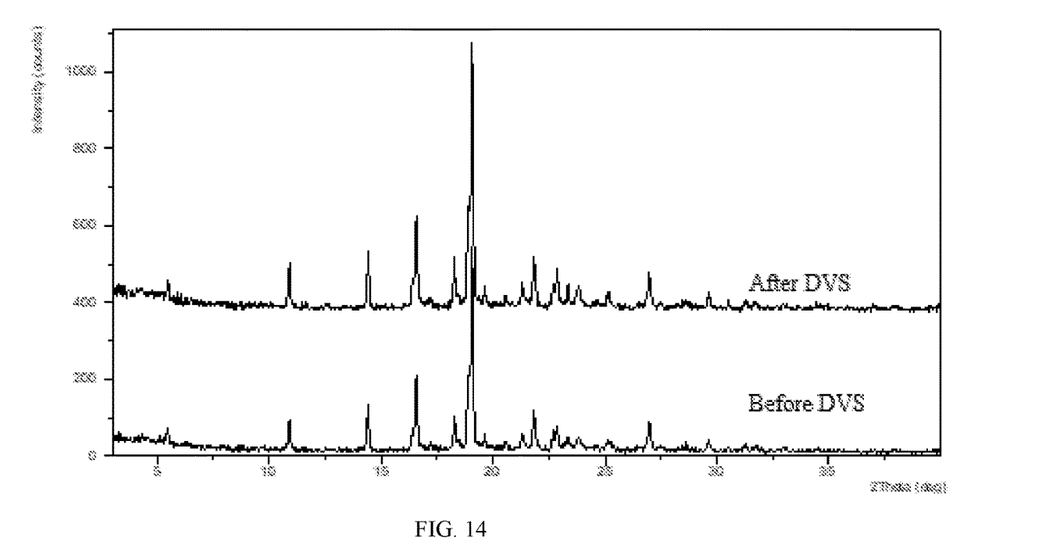
FIG. 14 shows an XRPD pattern overlay of Form G before and after DVS test.

The DVS plot of Form G is substantially as depicted in FIG. 12. The DVS plot of crystalline form of the prior art is substantially as depicted in FIG. 13. The XRPD overlay of Form G is substantially as depicted in FIG. 14, which shows no crystalline form change of Form G before and after DVS. The results in Table 7 show that the hygroscopicity of the crystalline form of the prior art is 2-7 times higher than that of Form G. The hygroscopicity of Form G is superior to that of the crystalline form of the prior art.

Example 8 Density of Form G

The density of powder is mainly referred to the bulk density and tapped density. The bulk density refers to the density obtained by dividing the mass of the powder by the volume of the powder in the container. The tapped density is obtained by dividing the mass of the powder by the volume of the powder which is tapped to the tightest state.

About 500 mg of Form G and the crystalline form of the prior art are added into a 5-mL measuring cylinder to measure the bulk volumes. The bulk density was calculated according to the equation: bulk density $\rho_0$=powder mass/bulk volume. The samples were tapped 1250 times to make them in the tightest state and the tapped volumes were recorded. The tapped density was calculated according to tapped density $\rho_f$=powder mass/tapped volume. The results in Table 8 show that the bulk density of Form G is more than 4 times than that of the crystalline form of the prior art, and the tapped density of Form G is more than 3 times than that of the crystalline form of the prior art. The density of Form G is remarkably superior to that of the crystalline form of the prior art.

TABLE 8

| Crystalline form | Bulk density ($\rho_0$, g/mL) | Tapped density ($\rho_f$, g/mL) |
|---|---|---|
| Crystalline form of the prior art | 0.133 | 0.204 |
| Form G | 0.538 | 0.614 |

Example 9 Flowability of Form G

Compressibility is usually used to evaluate the flowability of powder and granular intermediates during the formulation process, and is known as compressibility index (c). Compressibility index test method is as follows: a certain amount of powder was added into a measuring cylinder and bulk volume was recorded. Then the powder was tapped to make it in the tightest state, and the tapped volume was recorded. The bulk density ($\rho_0$), tapped density ($\rho_f$) were calculated, and compressibility index was calculated according to $c=(\rho_f-\rho_0)/\rho_f$. Compressibility index, also known as Carr index, is an important index for evaluating flowability.

The test method of Compressibility index is as follows: Compressibility index was calculated according to bulk density $\rho_0$ and tapped density $\rho_f$ of Form G and the crystalline form of the prior art with $c=(\rho_f-\rho_0)/\rho_f*100\%$. Criteria of flowability is shown in Table 9.

TABLE 9

| Compressibility index (%) | Flowability |
|---|---|
| ≤10 | Excellent |
| 11-15 | Good |
| 16-20 | Fair |
| 21-25 | Passable |
| 26-31 | poor |
| 32-37 | Very poor |
| >38 | Very, very poor |

Flowability evaluation results of Form G and the crystalline form of the prior art are shown in Table 10, which indicate that flowability of Form G is remarkably superior to that of the crystalline form of the propr art

TABLE 10

| Crystalline form | Bulk density ($\rho_0$, g/mL) | Tapped density ($\rho_f$, g/mL) | Compressibility index (%) | Flowability |
|---|---|---|---|---|
| Crystalline form of the prior art | 0.133 | 0.204 | 35.0 | Very poor |
| Form G | 0.538 | 0.614 | 12.5 | Good |

Example 10 Adhesiveness of Form G 30 mg of Form G and the crystalline form of the prior art were weighed and added into the dies of φ8 mm round tooling, tabletted at 10 KN and held for 30 s. The amount of material sticking to the punch was weighed. The compression was repeated twice and the cumulative amount, maximum amount and average amount of material sticking to the punch during the compression process were recorded. Detailed experimental results are shown in Table 11, which indicate that the sticking amount of the crystalline form of the prior art is more than 3 times than that of Form G, and the adhesiveness of Form G is superior to that of the crystalline form of the prior art.

TABLE 11

| Crystalline form | Maximum amount (mg) | Average amount (mg) | Cumulative amount (mg) |
|---|---|---|---|
| Crystalline form of the prior art | 0.43 | 0.21 | 0.41 |
| Form G | 0.12 | 0.06 | 0.12 |

The examples described above are only for illustrating the technical concepts and features of the present disclosure, and intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure.

What is claimed is:

1. Crystalline Form G of Baricitinib of the formula:

wherein the crystalline Form G is characterized by a reflection X-ray powder diffraction pattern (CuKα radiation) comprising characteristic diffraction peaks at angles (° 2θ) of 10.9°±0.2° 2θ, 16.5°±0.2° 2θ, and 19.0°±0.2° 2θ.

2. The crystalline Form G according to claim 1, wherein the crystalline Form G is further characterized by a reflection X-ray powder diffraction pattern (CuKα radiation) comprising one, two, or three additional characteristic diffraction peaks at angles (° 2θ) selected from the group consisting of 14.4°±0.2° 2θ, 18.2°±0.2° 2θ, and 21.8°±0.2° 2θ.

3. The crystalline Form G according to claim 1, wherein the crystalline Form G is further characterized by a reflection X-ray powder diffraction pattern (CuKα radiation) comprising one, two, or three additional characteristic diffraction peaks at angles (° 2θ) selected from the group consisting of 22.8°±0.2° 2θ, 23.8°±0.2° 2θ, and 26.9°±0.2° 2θ.

4. A pharmaceutical composition comprising one or more pharmaceutically acceptable carriers, diluents, or excipients and a therapeutically effective amount of the crystalline Form G according to claim 1.

5. A method for inhibiting Janus kinase activity in a subject, comprising administering to the subject in need thereof a therapeutically effective amount of the crystalline Form G according to claim 1.

6. The method according to claim 5, wherein the subject has an autoimmune disease.

7. The method according to claim 6, wherein the autoimmune disease is rheumatoid arthritis.

8. A process for preparing crystalline Form G of Baricitinib of the formula:

according to claim 1, wherein the process comprises the following steps:
(1) heating crystalline Form E of Baricitinib to a temperature in the range of room temperature to 212° C. at a rate of 10° C. per minute, to obtain a solid;
(2) maintaining the solid provided in step (1) at 212° C. for a period in the range of one minute to ten minutes; and
(3) cooling the solid provided in step (2) to room temperature, to obtain the crystalline Form G of Baricitinib according to claim 1.

9. The process according to claim 8, wherein the process comprises maintaining the solid provided in step (1) at 212° C. for a period of ten minutes.

\* \* \* \* \*